United States Patent [19]

Toye et al.

[11] Patent Number: 4,978,334
[45] Date of Patent: Dec. 18, 1990

[54] APPARATUS AND METHOD FOR PROVIDING PASSAGE INTO BODY VISCUS

[76] Inventors: Frederic J. Toye, 718 A James St.; James D. Weinstein, 1109 Woodland Dr., both of Bridgeport, W. Va. 26330

[21] Appl. No.: 241,948

[22] Filed: Sep. 8, 1988

[51] Int. Cl.⁵ .............................................. A61M 5/00
[52] U.S. Cl. ...................................... 604/51; 604/164
[58] Field of Search ................ 604/165, 164, 170, 51; 128/305, 343, 200.26, 207.14, 207.15

[56] References Cited

U.S. PATENT DOCUMENTS

| | | |
|---|---|---|
| 300,285 | 6/1884 | Russell . |
| 1,063,750 | 6/1913 | Townsend . |
| 2,224,575 | 12/1940 | Montalvo-Guenard . |
| 2,786,469 | 3/1957 | Cohen . |
| 2,865,374 | 12/1958 | Brown et al. . |
| 2,873,742 | 2/1959 | Shelden . |
| 2,991,787 | 7/1961 | Shelden et al. . |
| 3,001,522 | 9/1961 | Silverman . |
| 3,132,645 | 5/1964 | Gasper . |
| 3,137,298 | 6/1964 | Glassman . |
| 3,182,663 | 5/1965 | Abelson . |
| 3,330,278 | 7/1967 | Santomieri . |
| 3,384,087 | 5/1968 | Brummelkamp . |
| 3,511,243 | 5/1970 | Toy . |
| 3,659,612 | 5/1972 | Shiley et al. . |
| 3,688,773 | 9/1972 | Weiss . |
| 3,742,958 | 7/1973 | Rundles . |
| 3,788,326 | 1/1974 | Jacobs . |
| 3,794,036 | 2/1974 | Carroll . |
| 3,854,484 | 12/1974 | Jackson . |
| 4,096,860 | 6/1978 | McLaughlin . |
| 4,106,506 | 8/1978 | Koehn et al. . |
| 4,239,042 | 12/1980 | Asai . |
| 4,250,881 | 2/1981 | Smith . |
| 4,364,391 | 12/1982 | Toye . |
| 4,471,778 | 9/1984 | Toye . |
| 4,531,935 | 7/1985 | Berryessa . |
| 4,581,019 | 4/1986 | Curelaru et al. . |
| 4,593,687 | 6/1986 | Gray et al. . |
| 4,622,968 | 11/1986 | Persson . |
| 4,629,450 | 12/1986 | Suzuki et al. . |
| 4,642,101 | 2/1987 | Krolikowski . |
| 4,643,188 | 2/1987 | Weiss . |
| 4,668,226 | 5/1987 | Omata et al. . |
| 4,677,978 | 7/1987 | Melker ............................ 128/207.14 |

FOREIGN PATENT DOCUMENTS 3015593  10/1981  Fed. Rep. of Germany .

OTHER PUBLICATIONS

Clinical Experience with Percutaneous Tracheostomy and Cricothyroidotomy in 100 Patients vol. 26, No. 11, F. J. Toye & J. D. Weinstein.

*Primary Examiner*—Stephen C. Pellegrino

[57] ABSTRACT

An apparatus and method for providing a percutaneous or non-dissection passage into a body cavity or hollow viscus. A needle is attached to a syringe for insertion within the body cavity. Operation of the syringe confirms proper location of the needle within the body cavity. The needle is coaxially fitted within a dilator which is coaxially fitted within a tube. A leader portion of the dilator follows the insertion path defined by the needle to dilate the tissues for entry of the larger portions of the dilator and the tube. The needle and dilator can be slidably withdrawn to leave the tube in position. Various dilator leader structures are disclosed.

1 Claim, 2 Drawing Sheets

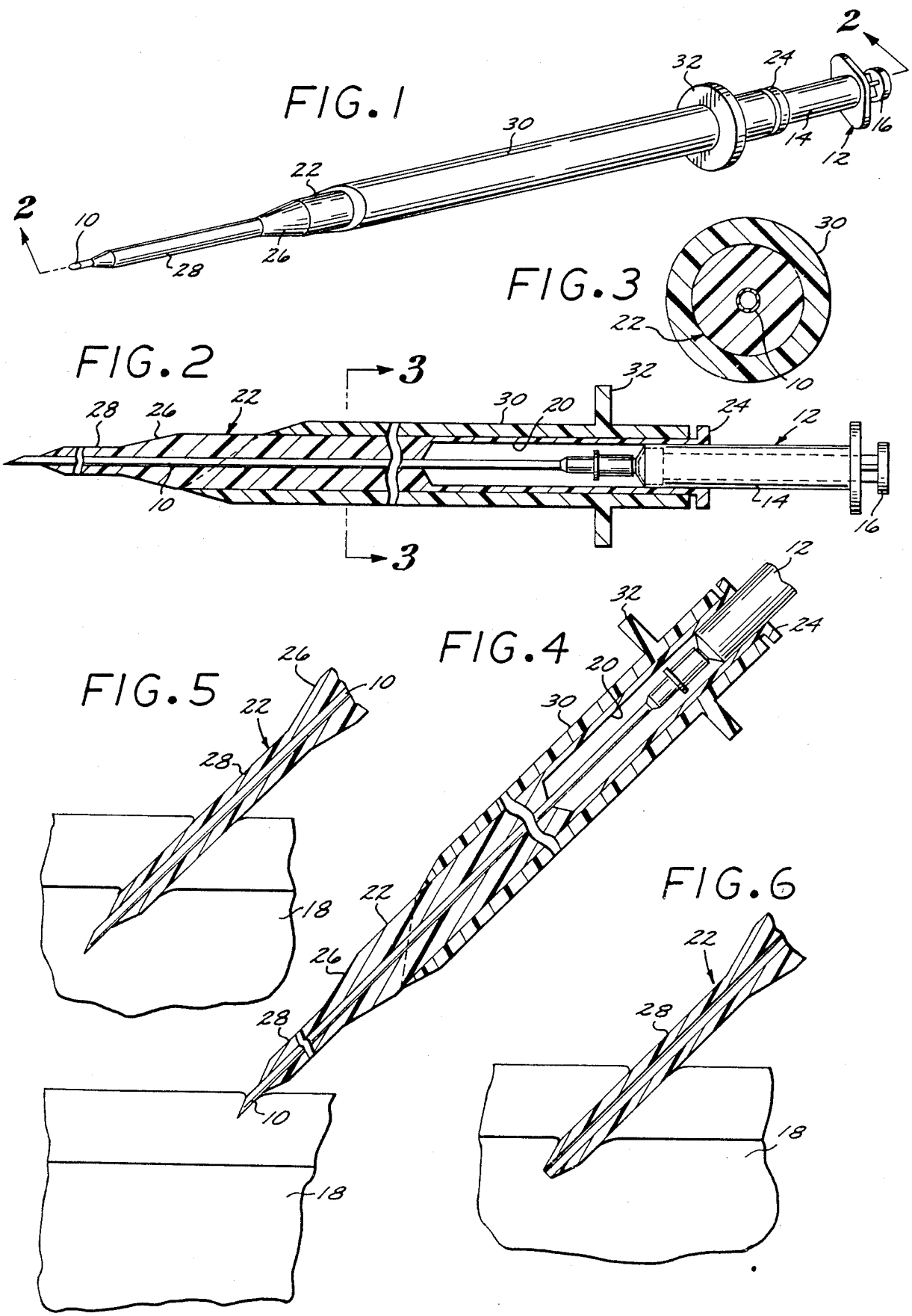

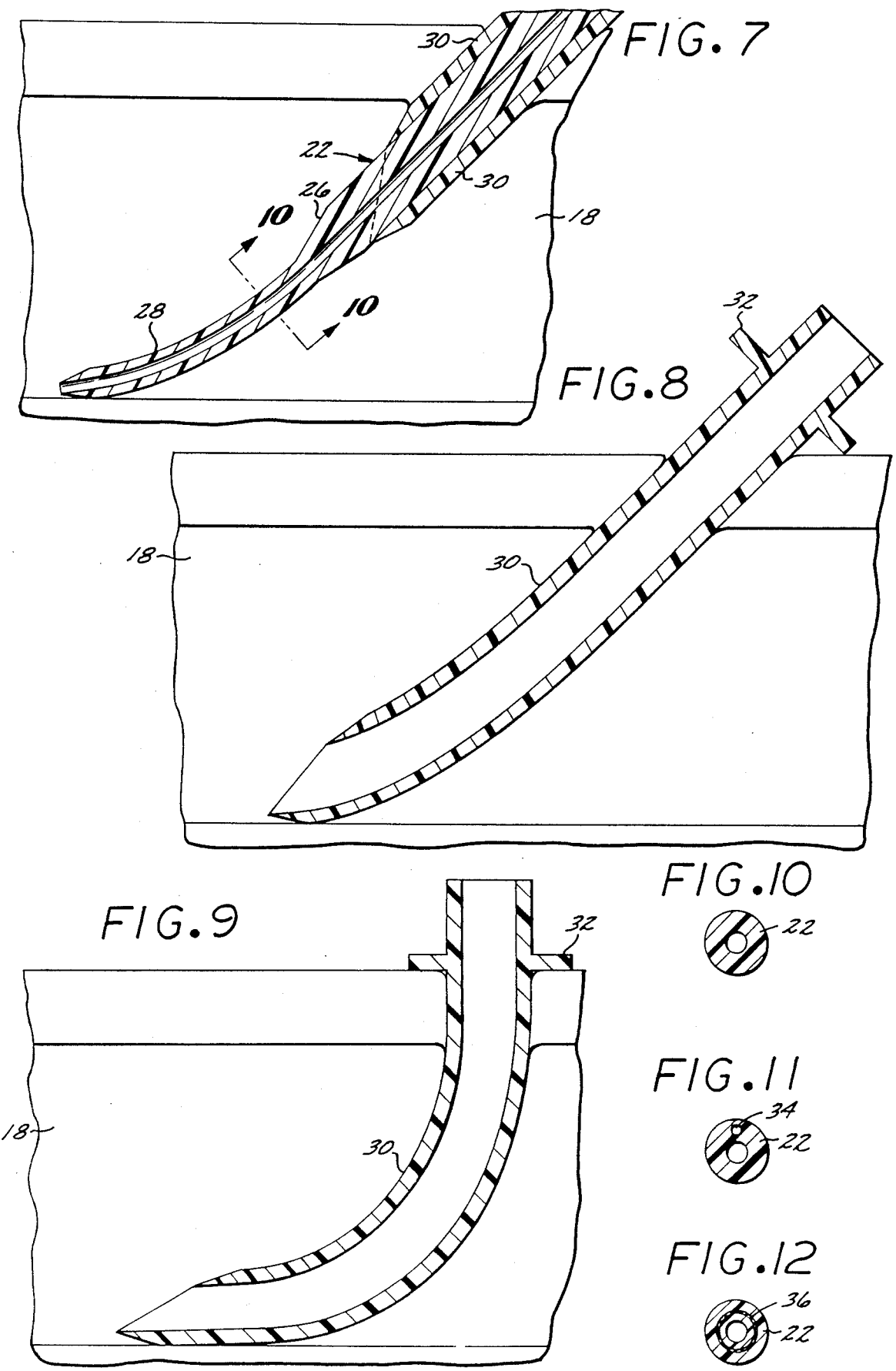

APPARATUS AND METHOD FOR PROVIDING PASSAGE INTO BODY VISCUS

BACKGROUND OF THE INVENTION

1. Field of the Invention:

The present invention relates to an apparatus and method for performing a percutaneous or non-dissection procedure to establish a passage or entry into a body cavity or viscus.

2. Description of the Prior Art

A number of devices have been advanced for non-dissection establishment of passages into a body cavity or hollow viscus, particularly for tracheostomies. Such devices are normally preferable to dissection procedures, which require considerable surgical skills in that many blood vessels are involved which tend to bleed profusely during a dissection procedure.

U.S. Pat. No. 3,511,243 (Toye) discloses a method and apparatus which utilizes a dilator to which a flexible leader is separably attached. First, a hollow needle is inserted into the trachea, and the leader is then passed through the needle and into the trachea, following which the needle is withdrawn. An inner guide telescoped within an outer guide is attached to the leader and both are forced into the trachea along the path defined by the leader. The inner guide is then withdrawn, removing the leader with it. A breathing tube is then inserted through the outer guide into the trachea, following which the outer guide is withdrawn, leaving the breathing tube in position. The method involves a precise sequence of steps, and the sequence of use of the various components requires appreciable training.

U.S. Pat. No. 4,364,391 (Toye) discloses a related but somewhat less involved procedure. A slotted outer needle and an inner needle telescoped within the outer needle are inserted into the trachea by means of a syringe attached to the inner needle. The syringe and attached inner needle are withdrawn, leaving the slotted outer needle in place. A leader is fed through the needle and into the trachea. The leader is attached to a dilator which is telescopably received within an outer trachea tube. In a simultaneous action, the needle is withdrawn from the trachea, and the leader is laterally stripped away from the needle through its slot, leaving the leader in the trachea. Using the leader as a guide, the dilator and trachea tube are forced into the trachea, following which the dilator and its attached leader are withdrawn, leaving the trachea tube in position. Use of the slotted outer needle allows fixed attachment of the leader to the dilator, as compared to the arrangement of U.S. Pat. No. 3,511,423. However, the procedure nevertheless requires significant training of personnel in the precise steps to be followed.

U.S. Pat. No. 4,471,778 (Toye) is related to and is an outgrowth of the procedures set forth in the above-identified '243 and '391 patents. The method and apparatus of this patent eliminates one of the two needles of the prior patent, instead using a single splittable needle which receives the dilator leader. More particularly, a syringe is used to insert the splittable needle, following which a leader is inserted through the splittable needle into the trachea. The leader is attached to a dilator which is laterally disposed through an opening in the side of a breathing tube, and then out the end of the breathing tube. After insertion of the leader, the needle is split and removed. Next, the dilator is thrust into the trachea, carrying the breathing tube with it. Finally, the dilator and attached leader are laterally removed from the side opening in the breathing tube, leaving the breathing tube in position within the trachea. The use of the splittable needle and the lateral entry of the dilator into a side opening in the breathing tube simplified the procedures of the previously mentioned patents, but certain complexities in procedure remained.

The present invention is an extension of the foregoing inventions, and was developed to reduce the number of component parts of the apparatus and to simplify the method of use.

SUMMARY OF THE INVENTION

According to the present invention an apparatus and method are provided which utilize a single needle attached to a syringe for insertion of the needle into the body cavity or hollow viscus. The syringe gives immediate indication of penetration of the body cavity through aspiration, the syringe plunger being readily movable outwardly upon such penetration.

The needle is located telescopically within a central passage or bore of a dilator and extends out of a tapered end of the dilator. A trachea, breathing or airway tube telescopically receives the dilator.

After the needle and the distal extremity of the associated dilator penetrate the body cavity, the syringe and needle are slidably removed from the dilator, leaving the dilator partially extending into the trachea. The dilator and surrounding breathing tube are then thrust further into the cavity along the path defined by the end of the dilator. The dilator is made of a flexible material so that its elongated distal extremity can serve as a leader for the breathing tube.

Once the tube has penetrated the cavity the dilator is removed through the open proximal end of the tube, leaving the tube in position within the body cavity. This is followed by final insertion of the breathing tube into better operating position.

The distal extremity of the breathing tube is preferably made of flexible material capable of deforming in conformity with the body cavity to prevent trauma to the surrounding tissue. The component plastic material of the trachea or breathing tube may have a "memory" so that when freed from the straightening constraint of the dilator it will curve to its originally formed, more physiologic "C" shape, as illustrated.

The present apparatus significantly reduces the number and complexity of the procedural steps necessary to perform a tracheostomy or the like.

Other aspects and advantages of the present invention will become apparent from the following more detailed description taken in conjunction with the accompanying drawings.

BRIEF DESCRIPTION OF THE DRAWINGS

FIG. 1 is a perspective view of the assembled apparatus;

FIG. 2 is an enlarged longitudinal cross sectional view of the apparatus of FIG. 1, the length of the showing being reduced to conserve drawing space;

FIG. 3 is an enlarged view taken along the line 3-3 of FIG. 2;

FIG. 4 is a view similar to FIG. 2, but illustrating the apparatus as it would appear upon initial penetration of the tracheal lumen by the needle in a tracheostomy procedure, the tracheal lumen being illustrated diagrammatically for simplicity;

FIG. 6 is a partial showing of the dilator partially penetrating the tracheal lumen, after the needle and associated syringe have been removed;

FIG. 7 is an enlarged view, similar to the showing of FIG. 6, but illustrating the dilator inserted into the tracheal lumen sufficiently that the distal extremity of the dilator, which serves as the leader, is deformed by a wall of the lumen;

FIG. 8 is a longitudinal cross sectional view of the breathing tube partially inserted into the tracheal lumen, and following removal of the dilator;

FIG. 9 is a view similar to FIG. 8, but illustrating full insertion of the breathing tube;

FIG. 10 is an enlarged view taken along the line 10-10 of FIG. 7;

FIG. 11 is a view similar to FIG. 10, but illustrating a leader in the form of a wire embedded in and made integral with the dilator tip; to stiffen the structure.

FIG. 12 is a view similar to FIG. 10, but illustrating yet another form of leader employed with the dilator.

DESCRIPTION OF THE PREFERRED EMBODIMENTS

As will be seen from the description which follows, the present method and apparatus will be described with reference to tracheostomy procedures. However, with relatively minor and obvious modifications the method and apparatus are equally useful in providing a passage or entry into any other body cavity or hollow viscus, such as in a thoracotomy to provide an opening into the thorax, a peritoneoscopy to provide an opening into the abdominal cavity, or a cystostomy to provide an opening into the bladder. Accordingly, the specific reference hereinafter to tracheostomies is merely exemplary.

The present apparatus and method are, like the apparatus of the previously identified patents of Toye, adapted to be employed to perform a percutaneous tracheostomy, in contrast to a dissection tracheostomy which involves extensive surgical cutting of tissues and attendant skill. The present apparatus and method do not require the same level of skill and are therefore adapted for use in emergency situations by persons not having extensive surgical training.

In performing a tracheostomy, the initial steps of the present method utilize a single needle in association with a syringe. The syringe plunger is withdrawn when the needle is located within the tracheal lumen to confirm proper needle penetration which is critical to a successful tracheostomy. An important feature of the present method and apparatus is the coaxial mounting of the needle within a dilator, and the coaxial mounting of the dilator within a breathing tube. As will be seen, the needle provides a path for insertion of the dilator tip, and the dilator tip serves as a flexible leader for the breathing tube. The coaxial arrangement allows the needle to be axially separated from the dilator and withdrawn from the trachea. The remaining leader portion of the dilator is thereafter movable inwardly to progressively enlarge or expand the needle opening and carry with it the breathing tube.

As will be apparent to those skilled in the medical arts, the various components of the present apparatus are configured and dimensioned to suit the size and condition of the patient, the dimensions being made smaller in the case of children, for example. In addition, it is a feature of the present invention that the trachea tube is insertable far enough to reach the deeply located trachea characteristic of some individuals.

The figures of the drawings generally follow the sequence of steps which characterize the practice of the present method.

With reference to FIG. 1, the present apparatus comprises an elongated needle 10 having a sharpened, wedge-shaped distal tip to facilitate penetration of the trachea and associated tissue and cartilage. The needle preferably includes a central bore in communication with an attached conventional syringe 12 having the usual barrel 14 and plunger 16. As previously indicated, when the needle 10 penetrates the tracheal lumen, which is designated generally by the numeral 18, such penetration can be confirmed by withdrawing the plunger 16 to draw air from the trachea.

The syringe barrel 14 and needle 10 are slidably receivable, respectively, within the open proximal end of an elongated recess 20 in a dilator 22, and within a dilator bore in communication with the recess. A stop means or flange 24, whose function will be described, is integral with the dilator end portion.

The dilator is of substantially uniform diameter at its proximal extremity and then tapers at 26, as seen in FIG. 2, to an elongated lesser diameter distal extremity 28 having a tapered end. The tapered end is located adjacent the tip of the needle where it protrudes from the dilator bore in the initial position of the needle.

The dilator 22 is preferably made of any suitable flexible plastic material, such as polyethylene or the like, such that the distal extremity of the dilator can bend and function as a leader.

The dilator, is telescopically or concentrically received within the central bore of an elongated trachea, airway or breathing tube 30. As seen in the drawings, the central bore is unobstructed to permit unrestricted air flow during use of the tube for breathing. The tube 30 is engaged at one end by the dilator flange 24. This locates the dilator in proper axial position within the tube. The tube 30 also includes a stop means in the form of a circular collar or flange 32 which limits the degree of penetration of the breathing tube into the tracheal lumen.

The distal end of the breathing tube 30 is feathered and cut on a bias to facilitate its entry into the tracheal lumen. The feathered edge of the bias portion generally coincides with the taper 26 of the dilator 22 so that a smooth transition is provided between the taper 26 and the outer surface of the breathing tube 30.

Like the dilator 22, the breathing tube 30 is also preferably made of a flexible plastic material capable of deforming or bending to conform to the tracheal lumen to avoid trauma to the adjacent tissues in situ. The plastic material is preferably characterized by a "memory". Thus, it would be molded in a gentle curvilinear or "c" shape. When it is sleeved over the dilator it would be essentially straight. Upon renewal of the dilator, the breathing tube in situ would then reassume its originally molded in "c"-shape, which is more physiologic in situ.

Use of the apparatus just described is extremely simple and straightforward. Its use is therefore well within the capability of regular health care emergency specialists. In performing a tracheostomy for example, the needle 10, dilator 22 and tube 30 are assembled in the manner illustrated in FIG. 2. The needle 10 is next inserted into the area adjacent the tracheal lumen 18, as seen in FIG. 4, and the insertion is continued until the lumen is penetrated by both the needle 10 and the extremity 28, as seen in FIG. 5. Such penetration is signaled by freedom of the syringe plunger to withdraw air from the trachea through the needle, as previously mentioned.

The syringe 12 is then removed from the dilator, as seen in FIG. 6, leaving the dilator and associated breathing tube 30 in position.

The dilator and tube are then further urged into the trachea, as seen in FIG. 7. During such insertion the tapered surfaces of the dilator and tube help to enlarge the initial passage provided by the dilator extremity 28, with bleeding being minimized by the tamponade effect of the forced apart tissues.

The dilator is next withdrawn, as seen in FIG. 8, leaving the breathing tube 30 in position. Finally, the tube may be thrust farther into operative position within the trachea, as seen in FIG. 9, bending conformably to the walls of the tracheal lumen, as previously described.

If desired, a respirator (not shown) can now be attached to the breathing tube and operated in the usual fashion, as will be obvious to those skilled in the art.

In the embodiment just described the distal extremity of the dilator serves as the leader to facilitate entry of the larger diameter portions of the dilator and the breathing tube, its flexibility enabling it to bend and align itself with the trachea.

FIG. 11 illustrates an alternative embodiment in which a plastic coated wire 34 or the like is molded into the with the material of the dilator extremity, as illustrated, or molded into the dilator and itself constituting the extremity of the dilator. This provides a leader having increased structural rigidity, but one which is still bendable to conform to the lumen walls.

FIG. 12 illustrates yet another embodiment of a dilator leader. The leader in this case is defined by a flexible, bendable coaxial sleeve braided of plastic coated wire 36 adapted to project coaxially of the inserted needle.

From the foregoing it will be apparent that the coaxial arrangement of the needle, dilator and breathing tube significantly simplify the insertion procedure in a tracheostomy procedure or the like. The arrangement enables the needle to carry the dilator and the dilator to carry the breathing tube in a manner enabling these elements to be easily separated in reverse order, leaving the breathing tube in a properly inserted position.

Various modifications and changes may be made with regard to the foregoing detailed description without departing from the spirit of the invention, particularly with respect to procedures other than tracheostomies.

I claim:

1. A percutaneous non-dissection method for providing a passage into a body cavity, the method comprising the steps of:
   locating a hollow needle and attached syringe within an elongated flexible dilator, with the needle slidably disposed through and extending out of a central bore of the dilator;
   locating the dilator and needle in coaxial relationship to the cylinder interior of a tube;
   forming a passage into the body cavity by insertion of the needle and the distal extremity of the dilator into the cavity;
   operating the syringe to withdraw air from the cavity to establish penetration of the cavity by the needle;
   slidably withdrawing the needle and syringe from the dilator;
   urging the dilator and the distal extremity of the tube into the cavity along the passage defined by the needle and the distal extremity of the dilator; and
   slidably withdrawing the dilator from the tube.

* * * * *